United States Patent [19]

Picha

[11] Patent Number: 5,158,571
[45] Date of Patent: Oct. 27, 1992

[54] TISSUE EXPANDER AND METHOD FOR EXPANDING TISSUE

[76] Inventor: George J. Picha, 6554 Beechwood Dr., Independence, Ohio 44131

[21] Appl. No.: 748,258

[22] Filed: Aug. 21, 1991

Related U.S. Application Data

[63] Continuation-in-part of Ser. No. 491,225, Mar. 9, 1990, abandoned.

[51] Int. Cl.$^5$ ............................................. A61F 2/02
[52] U.S. Cl. ..................................... 623/11; 606/192; 604/96; 623/8
[58] Field of Search ................... 623/8, 7, 11; 604/96; 606/192

[56] References Cited

U.S. PATENT DOCUMENTS

| | | | |
|---|---|---|---|
| 3,366,975 | 2/1968 | Pangman | 623/8 |
| 4,217,889 | 8/1980 | Radovan et al. | 128/1 R |
| 4,272,855 | 6/1981 | Frey | 623/16 |
| 4,531,244 | 6/1985 | Hamas | 623/8 |
| 4,574,780 | 3/1986 | Manders | 128/1 R |
| 4,608,052 | 8/1986 | Van Kampen et al. | 623/22 |
| 4,643,733 | 2/1987 | Becker | 623/8 |
| 4,651,717 | 3/1987 | Jakubczak | 128/344 |
| 4,671,255 | 6/1987 | Dubrul et al. | 128/1 R |
| 4,955,909 | 9/1990 | Ersek et al. | 623/8 |
| 5,002,572 | 3/1991 | Picha | 623/11 |

OTHER PUBLICATIONS

Picha and Siedlak, "Ion-Beam Microtexturing of Biomaterials", *Medical Device and Diagnostic Industry*, vol. 6, No. 4, Apr. 1984.
Dow Corning Wright, "Silastic MSI Tissue Expander, H. P.", Catalog P.S. 559-1290, 1990.
Cherup et al. "Measurement of Capsular Contracture: The Conventional Breast Implant and the Pittsburgh Implant" *Plastic and Reconstructive Surgery*, Dec., 1989, pp. 893-902.
S. R. Taylor, "The Soft Tissue Response to an Ion Beam Textured Surface," Case Western Reserve University, May 1980, Master's Thesis.
E. A. Powell, "Changes in the Subcutaneous Tissue Response Cause by Implant Compliance and Surface Morophology," Case Western Reserve University, May, 1982, Master's Thesis.
"Effect of Ion-Milled Microstructure on Capsule Formation in Silicones," European Congresson Biomaterials, Sep. 14-17, 1986, Bologna, Italy, p. 125.
"The Soft Tissue Response to Ion-Milled Surface Structures," Transaction of the Society for Biomaterials, 13th Annual Meeting, Jun. 3-7, 1987, New York, NY, p. 267.
G. J. Picha & D. F. Gibbons, "Final Report of the Effect of Controlled Surface Morphology on the Subcutaneous Tissue Response," NASA Report CR-165319, Grant NAG 3-12, Mar. 1981.

*Primary Examiner*—David Isabella
*Assistant Examiner*—D. S. Brittingham
*Attorney, Agent, or Firm*—Pearne, Gordon, McCoy & Granger

[57] ABSTRACT

A tissue expander is disclosed. Extending from the outer surface of the tissue expander are a plurality of projections of specific combinations of height and width dimensions selected from the groups consisting of (1) approximately 750 microns high and approximately 250 microns wide and (2) approximately 1,600 microns high and approximately 800 microns wide. Preferred edge-to-edge spacing distance between adjacent projection and center-to-center spacings between adjacent projections are also disclosed. A method of expanding tissue utilizing the disclosed tissue expander is also disclosed.

20 Claims, 2 Drawing Sheets

TISSUE EXPANDER AND METHOD FOR EXPANDING TISSUE

This application is a continuation-in-part of application Ser. No. 07/491,225, filed Mar. 9, 1990, abandoned.

BACKGROUND OF THE INVENTION

The present invention relates in general to tissue expanders and in particular, to a surface morphology for a tissue expander and a method of expanding tissue and increasing nonclassical tissue response and/or altering the fibrous capsule in connection with tissue expansion utilizing such surface morphology, which method can reduce scar tissue.

DESCRIPTION OF RELATED ART

It is well-known that skin and its subcutaneous tissue can greatly be expanded in area if the expansion is accomplished gradually. The extension of the skin over a pregnant woman's abdomen is one example. Tissue expander devices or implants are well known in the art. These devices are temporarily implanted beneath the skin and subcutaneous tissue of humans or domestic animals, and may be gradually or slowly inflated by injection of saline (or similar liquids) for the purpose of causing the growth of a skin flap or enlargement; an increase in the overall surface area of the overlying skin. For a detailed description of tissue expanders, see U.S. Pat. Nos. 4,671,255; 4,651,717; 4,643,733; 4,574,780; and 4,217,889; the contents, including drawings, of which are hereby incorporated by reference in their entirety. Briefly summarized, a tissue expander comprises a surgically implantable, three-dimensional, inflatable bag or envelope or shell of flexible and typically stretchable material. The shell may have a top wall or extendable wall to increase the volume of the tissue expander and relatively firmer opposed bottom wall or back wall to determine the general direction of volume increase. A liquid is introduced or injected to gradually enlarge the shell and thereby cause the overlying skin and subcutaneous tissue to expand in area. A skin pocket or enlargement or flap is formed adjacent the extendable wall of the implanted tissue expander. At the conclusion of expansion and after the skin flap has formed, the shell is surgically removed and the fibrous capsule, if any, is typically excised or fragmented. A permanent, implantable device, such as a mammary implant or prosthesis, may thereafter be placed directly beneath the flap. Alternatively, the flap may be used to cover a defect directly adjacent to the place where the expansion occurred. The flap is pulled to extend it over the adjacent recipient area. The flap may also be used, after severance, for purposes of plastic surgery in other parts of the body.

When a foreign object is placed in the soft tissue (fascia, muscle, adipose, etc.) of a living body, that body generally attempts to eliminate or isolate the object. Microscopic objects may be engulfed by macrophages and eliminated. Objects Which are too large to be engulfed by macrophages tend to be isolated from the body by encapsulation in an envelope of collagen, which is commonly referred to as a fibrous capsule and which is scar tissue. A tissue expander is sufficiently large so as to fall into the latter class and, as a foreign object, is generally encapsulated by the body in a fibrous capsule, typically in a "classical" tissue response as more fully discussed and illustrated hereinafter.

A tissue expander, after subcutaneous or submuscular implantation, remains in place temporarily, i.e., typically between two and six months, generally about three months. It is typically located in the scalp, breast, trunk, and proximal portions of the extremities to expand the overlying tissue located there. Typical indications are for burn treatment, alopecia, cancer, large skin defects and breast reconstruction. About two weeks after implantation and intermittently or periodically, generally weekly, thereafter, injections of fluid, typically 50–60 cc of saline, are made into the device, either directly or remotely, to cause expansion to occur.

If a smooth-surfaced tissue expander is utilized, for example, for breast enlargement, scar tissue will typically be formed Within the first month, creating or forming a fibrous capsule. The formation of a fibrous capsule can lead to capsule contracture.

In capsule contracture, the fibrous capsule, over time, contracts and squeezes the tissue expander. Capsule contracture around a tissue expander can cause pain to the patient. It can also cause the expander to deform and lose its intended shape. This can be disadvantageous, particularly in some cases of breast enlargement. With breast enlargement, the tissue expander may be designed to expand differentially or into a specific breast-like shape to form a pocket of a specific shape. It is intended that the expander will be removed and a similarly-shaped permanent mammary implant will be implanted. If the expander is squeezed into the wrong shape during the enlargement process, the permanent implant may not properly fit into the pocket which was formed. Classical tissue response is associated with the problem of capsule contracture. Conversely, nonclassical tissue response, as more fully discussed and illustrated hereinafter, reduces the amount of scar tissue or alters its orientation and is believed to be associated with less incidence of capsule contracture and/or less severity of capsule contracture. Smooth-surfaced tissue expanders generally lead to a classical tissue response, which, as noted above, is associated with capsule contracture.

A mammary implant is a prosthesis for the human breast. It is generally intended to be implanted permanently. As used herein, a mammary implant is not inflated, or intended to be inflated, after implantation to cause tissue expansion. Its size and volume is fixed prior to or during the procedure of initial implantation. It was known in the art to surround a mammary implant with an external layer of open-cell foam-type sponge material, generally open-cell polyurethane foam. The porosity of the outer layer permitted it to become invaded by body cellular tissue, thereby causing the implant to adhere to the wall of the chest and also to the covering skin and tissues. U.S. Pat. No. 3,366,975 is exemplimatic of this art, and the teachings of that patent are incorporated herein by reference in their entirety.

While polyurethane foam-covered implants permitted tissue ingrowth and thus implant anchoring, the external layer of polyurethane foam was documented to undergo delamination and degradation with subsequent capsule contracture, obviously an undesirable condition.

Some teachings in the art have taught the use of a plurality of projections or posts extending from the surface of an implant as a means to reduce the thickness of the fibrous capsule. However, none of these teachings explored the cooperation of the height, width and lateral spacing of projections with respect to the foregoing effect. These teaching include the following, all of which teachings are hereby incorporated herein by reference in their entirety.

U.S. Pat. No. 4,531,244 to Robert S. Hamas teaches a mammary prosthesis comprising an envelope covered by a plurality of posts. According to the Hamas patent, the posts provide and maintain space therebetween such that when the scar tissue or fibrous capsule contracts and compresses the posts, the underlying mammary prosthesis will have a space for displacement and deformation and will remain soft. Hamas taught posts having a depth between 1,000 and 10,000 microns (preferably between 1,000 and 5,000 microns) and having a width at the base between 1,000 and 10,000 microns (preferably between 1,000 and 5,000 microns).

However, as will be disclosed hereinafter, the posts taught by Hamas do not teach optimal combinations of height, width, and/or lateral spacing dimensions. This is probably due in part to the fact that the posts taught by Hamas are used principally as mechanical elements to space the scar tissue or fibrous capsule away from the implant surface and not as biological elements to inhibit growth in thickness of the fibrous capsule and/or organization or alignment of the fibrous capsule.

In a Master's Thesis by Shelton Ray Taylor, "The Soft Tissue Response to an Ion Beam Textured Surface", Case Western Reserve University, May, 1980, a study was conducted comparing smooth implants with textured surface implants. The textured surface implants had projections (a) 12 microns high and 4 microns wide; and (b) 31 microns high and 1 micron wide. The author of the thesis concluded that the textured surface implants were encapsulated by a thinner fibrous capsule at 8 weeks, when compared to a smooth surface implant, but that at 18 weeks there was no difference in capsule thickness between the textured and smooth surface implants.

In Picha and Siedlak, "Ion-Beam Microtexturing of Biomaterials", *Medical Device and Diagnostic Industry*, Vol. 6, No. 4, April, 1984, there is described the use of ion-beam milling to produce microprojections on the surface of soft tissue prostheses such as breast prostheses, and the use of such breast prostheses to reduce capsule contracture. However, no specific optimum size of projections is taught.

In a Master's Thesis by Elizabeth A. Powell, "Changes in the Subcutaneous Tissue Response Caused by Implant Compliance and Surface Morphology", Case Western Reserve University, May, 1982, it was taught that over the six week period following implantation, a textured surface of micropillars 150 microns high, 75 microns wide, with center-to-center spacing between adjacent micropillars of 150 microns, lead to the formation of a thinner fibrous capsule, when compared with a smooth-surfaced implant. However, no optimum range of micropillar sizes for the textured surface were tested, considered, evaluated, or taught.

U.S. Pat. No. 4,608,052 discloses the use of surfaces containing a plurality of posts on implants for use in the human body. However, this reference does not specifically suggest the use of such surface morphologies for tissue expanders. The reference does suggest the use of posts on surfaces of soft tissue implants, but does not teach any particular height as optimal for the posts and in fact teaches the height of the post as theoretically unlimited (Col. 5, lines 31-35). The '052 patent further teaches that the width of the post is preferably about 50 to 150 microns; and that the edge-to-edge distance between posts is preferably 50 to 150 microns (Col. 5, lines 36-43).

In an Abstract entitled "Effect of Ion-Milled Microstructure on Capsule Formation in Silicones", European Congress on Biomaterials, Sep. 14-17, 1986, Bologna, Italy, page 125, it is taught that the anatomy of the "classical" capsule is altered dramatically by surface projections greater than 100 microns in height, that when the diameter of a surface projection is greater than 500 microns it begins to interact with the body as a bulk surface and a classical capsule is formed. It further teaches that the number and proximity of blood vessels is greatest for projections that are less than 250 microns in diameter and spacing, but greater than 100 microns in height.

In an Abstract entitled "The Soft Tissue Response to Ion Milled Surface Structures", Transactions of the Society for Biomaterials, 13th Annual Meeting, Jun. 3-7, 1987, New York, N.Y., page 267, textured surface microstructuring is discussed. This Abstract implies that the preferred dimensions of projections on an implant surface are 100 microns wide and 500 microns high.

SUMMARY OF THE INVENTION

In accordance with the present invention, an improved surface morphology for a tissue expander is provided. The surface morphology comprises a supporting structure and a plurality of projections extending from the outer surface, said projections being of specific height and width dimensions which provide improved nonclassical tissue response and reduced thickness of the fibrous capsule. In nonclassical tissue response there is a reduced amount of scar tissue, more natural vascularity, blood vessels in closer proximity to the implant surface, and, it is believed, less incidence of capsule contracture and/or less severity of capsule contracture. It has now been discovered that unique combinations of height and width dimensions provide proper tissue penetration with reduction of classical response displayed by continuous or bulk flat surfaces as discussed more fully below.

In accordance with the invention, the projection height and width dimensions are selected from combinations of dimensions comprising (1) an approximate height of 750 microns and an approximate width of 250 microns and (2) an approximate height of 1,600 microns and an approximate width of 800 microns. The term "approximate" is defined below. The projection dimensions and spacing are mean values and variations within customary manufacturing methods will occur. A method of expanding tissue is disclosed. A method to reduce the amount of scar tissue and, it is believed, the incidence of capsule contracture around a tissue expander is also disclosed. The method comprises implanting a tissue expander with a surface morphology as described above. The surface morphology of the present invention can be utilized with tissue expanders as known in the art, including differential tissue expanders, such as disclosed in U.S. Pat. Nos. 4,574,780 and 4,651,717, the contents of which are incorporated herein by reference. The surface morphology can be utilized on a portion of a differential expander, but not on the entire surface, to achieve a differential result.

It has been shown that a tissue expander having a surface morphology in accordance with the present invention will result in a fibrous capsule which is thinner, more pliable, and more compliant. This is advantageous, since a thicker, less pliable, less compliant fibrous capsule frequently requires disruption and fragmentation before the expanded skin can be used. The presence of the scar tissue capsule makes the skin flap less compliant and harder to work with. Total excision of the capsule is sometimes required. Also, a thicker capsule makes it harder to expand the expander; more pressure is required to push back and expand the capsule. This slows the expansion process and typically makes expansion more painful. Thus, a thinner capsule leads to reduction in the amount of pain, accelerated rate of expansion, and reduced total pressure required for expansion.

It is most surprising that the improvements of the present invention are exhibited by distinct combinations of projection dimensions as opposed to projections of varying dimensions within a single continuous range of sizes. The reason for the disjunction of the inventive projection dimensions is not fully understood. However, it is believed to be related to the coaction of the projection height and width to provide adequate tissue penetration and sufficient spacing between the projections to accommodate the penetrated tissue without yielding a classical response as by simulation of a bulk or continuous flat surface of significant size.

A fuller understanding of the invention may be had by referring to the following description and claims taken in conjunction with the accompanying drawings.

DESCRIPTION OF THE PREFERRED EMBODIMENT

Figure 1:
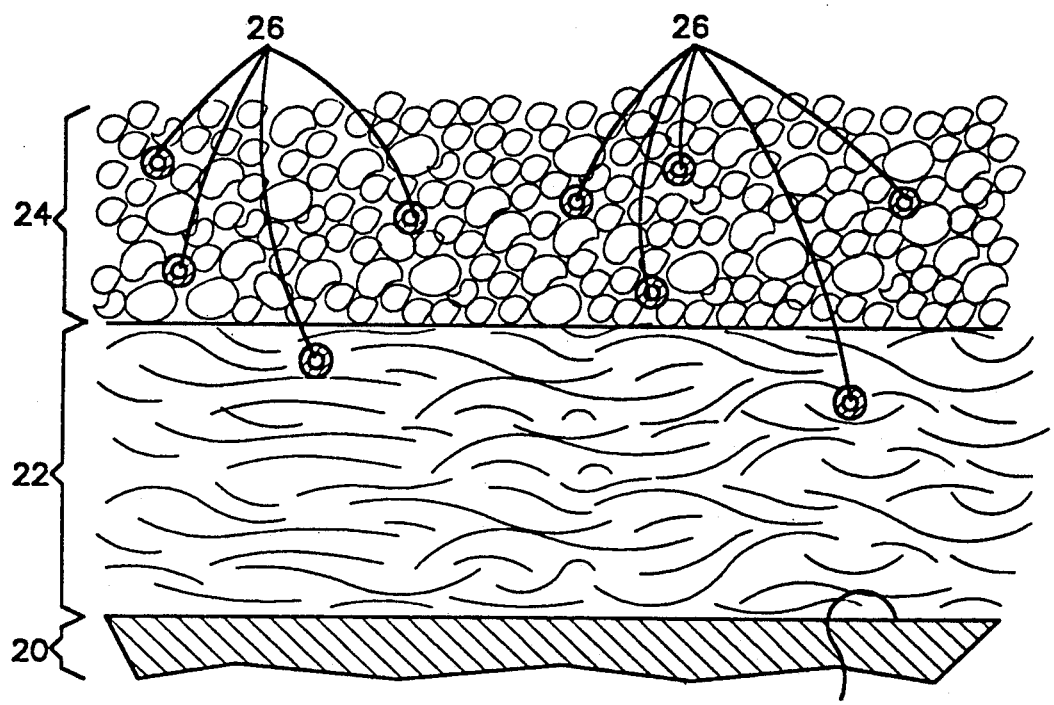
FIG. 1 is a magnified cross-sectional view of a classical fibrous capsule of collagen surrounding a smooth surface tissue expander or mammary implant.

FIG. 1 illustrates what is commonly referred to as the classical tissue response of the body to a smooth surface implant such as a smooth surface tissue expander or mammary implant. The surface of the implant such as a tissue expander is indicated at 21, and the bulk of the implant is partially indicated at 20. A relatively thick, dense fibrous capsule or layer 22 of highly oriented collagen forms around the implant after it is implanted. This layer 22 is scar tissue. Separated from the implant by the collagen layer are a plurality of fat cells 24 or fascia (not shown). Coursing through the fat cells are blood vessels 26. Some blood vessels 26 will also be found in the collagen layer, but these tend not to be in close proximity to the implant surface 21. Further, there is a relatively small amount of vascularization.

Figure 2:
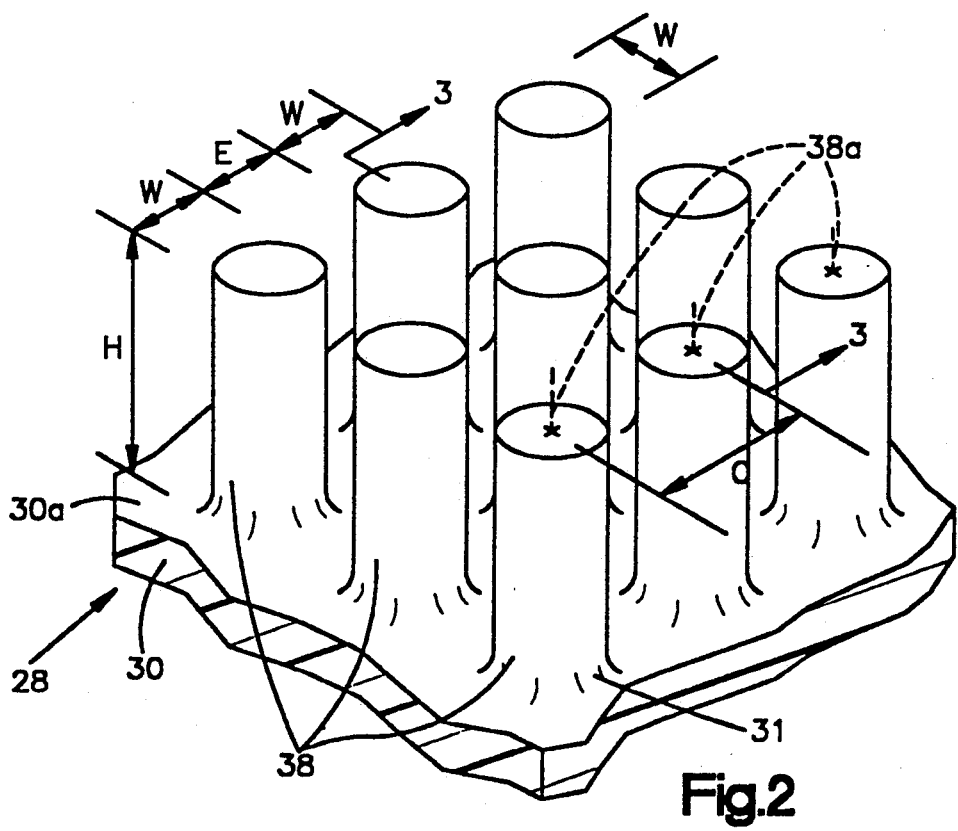
FIG. 2 is a magnified fragmentary perspective view of a tissue expander including a supporting structure having an outer surface provided with a surface morphology in accordance with the present invention, with the support structure of the tissue expander shown in cross-section.

FIG. 2 illustrates a portion of a tissue expander 28 including a supporting structure 30 which typically comprises an envelope, bag, or sack for receiving the liquid (usually saline) which is used to inflate the envelope. The inflation liquid can be injected percutaneously directly into the envelope or introduced through a remote port connected to the envelope via a tube or conduit. The envelope confines the inflation liquid. Tissue expanders can be made in many different sizes, shapes, and configurations. However, they must all have an outer surface or exterior surface which, after implantation, will be in contact with the bodily tissue. They must also be inflatable; that is, capable of being expanded or blown up or enlarged subsequent to implantation utilizing such means as an injected fluid, typically a liquid such as saline solution. The supporting structure 30 has an outer surface 30a provided with a surface morphology in accordance with the present invention. The surface morphology is provided at the outer surface 30a of the tissue expander and includes an array of outwardly extending projections 38 of relatively uniform size. The supporting structure 30 and the projections 38 can be made of any suitable medical grade material, preferably inert, as known in the art, including HP SILASTIC, a high performance silicone elastomer produced by Dow Corning, and other silicone and polymeric elastomers. The material must be flexible and preferably capable of stretching (stretchable) so that the envelope, when inflated with fluid, will enlarge. Frequently, the tissue expander will be constructed so that the top portion is stretchable while the bottom portion is relatively non-stretchable. In this way, most of the expansion of the device will occur towards the tissue to be expanded, not towards the interior of the body. The projections can be integrally formed with the supporting structure 30. For example, the projections may be formed by molding, by lasers, or by the use of ion-beam milling techniques, which are known in the art and are described in the related art references noted above.

The height (H) and width (W) of the projections 38 may be selected from the combinations of dimensions set forth above. As used in the specification and claims herein, the designation of a numerical value for a parameter such as height or width as "approximate" or "approximately" means a range of values from 10% less than the designated numerical value to 10% more than such value. Thus, an approximate height of 750 microns means a height in the range of from 675 to 825 microns.

The projections 38 are shown as circular in cross section and have a thickened portion or fillet 31 at the base. The thickened portion 31 provides a smooth joint between the projection 38 and the supporting structure 30 which tends to inhibit the development of stress risers. The thickened portion 31 also increases the strength of the attachment between the projection 38 and the supporting structure 30. The concave shape of the thickened portion distributes the stress forces, inhibiting cracking or fracturing.

The projections 38 are generally of a column or shaft-like shape. The projections may be of a tapered shape or a truncated-cone shape. The projections 38 are preferably circular in cross section, but may also be square, rectangular, triangular, rounded, or any other cross section provided that the ratio of (1) the longest lateral dimension through the centroid of the cross section to (2) the shortest lateral dimension through the centroid of the cross section, is no greater than about 2 to 1. Projections of non-circular cross section should preferably be thickened near the base for the reasons described above.

The top of the projection 38 is shown as flat. It can also be convex or concave. In FIG. 2 the projections are uniformly arrayed. They may be arranged in any suitable manner. The projections may extend from the vast majority of, from substantially all of, or from less than all of the outer surface area of the supporting structure. The projection should extend from a sufficient portion of the outer surface area of the supporting structure so as to be effective in tending to promote a nonclassical tissue response.

The projections 38 as shown in FIG. 2 have some sharp edges. Projections with a square or rectangular cross section have more sharp rectangular corners and edges. However, the corners and edges of a projection may be rounded or broken off or otherwise deformed. Some manufacturing techniques may result in these latter-described types of projections. Height is measured from the base of the projection at the supporting structure 30 to the highest point on the projection 38. Width is measured at the base of the projection 38 without allowing for the thickened portion 31. If the projection is of a tapered, cone, or non-regular shape, an average width may be used. If the projection is circular in cross section, the diameter is the width. If the projection is square or about square in cross section, the edge length is the width. Otherwise, the width is deemed to be the average of (1) the longest lateral dimension through the centroid of the cross section and (2) the shortest lateral dimension through the centroid of the cross section.

A lateral spacing (E) corresponds with the edge-to-edge distance between projections. It should be understood that the lateral spacing (E) indicates the clearance or distance between the major adjacent surface portions of neighboring projections. Accordingly, a lateral spacing (E) may be used to characterize, among others, projections having rounded edges or circular cross-sections. If the lateral spacing (E) is too small, the projections will become crowded together and act as a bulk or continuous flat surface. If the lateral spacing (E) is too large, the body again begins to treat the implant as a continuous flat surface. The height, width, lateral spacing (edge-to-edge), and center-to-center distances set forth in the specification and claims herein are measured when the supporting structure 30 is flat or relatively flat and the elastomeric material forming the supporting structure is in an unstretched, unexpanded, unstressed condition. It is understood that as the tissue expander envelope is inflated but without stretching, the tips of the projections will spread apart slightly due to the curvature of the supporting structure. It is believed that as the tissue expander is inflated such that the supporting structure 30 begins to stretch and enlarge laterally, the height and width dimensions of the projections do not change materially or significantly. The edge-to-edge and center-to-center distances may increase noticeably, but it is believed that this does not affect the performance of the tissue expander, since generally the expander is not expanded for two weeks after implantation, and only incrementally thereafter, and the scar tissue or capsule, to the extent it forms, is largely or significantly in place within one month. It is believed that the projections, among other things, disrupt collagen formation during this period. As the expander is expanded, the projections are affirmatively or positively pushed or urged into the surrounding tissue, thus forceably and pressureably engaging the tissue. The expander thus applies positive pressure to deform the tissue and cause it to increase in area. This positive pushing or urging provides enhanced tissue penetration over what would be achieved by means of a non-inflatable implant. A tissue expander of the present invention may be increased in volume after implantation, for example, from an original size of 100 cc to an enlarged size of 1,000 cc. A tissue expander of the present invention for the breast is typically increased in volume after implantation from 100 cc to 500–700 cc.

The preferred width to lateral spacing (W:E) ratio is between 1:0.4 and 1:5. For a 250 micron wide projection, the lateral spacing may range from 100 to 1,250 microns. In the case of an 800 micron wide projection, the lateral spacing range is from 320 to 4,000 microns. In the case of the 250 micron wide projection, the more preferred W:E radio is about 1:1. In the case of the 800 micron wide projection, the more preferred W:E ratio is about 1:0.5.

Each of the projections has a central axis or center line 38a. In the illustrated embodiment, the central axis 38a passes through the centroid of the projection 38 and is an axis of symmetry. The center-to-center spacing (C) between adjacent projections is equal to the width (W) plus the lateral spacing (E). Accordingly, the preferred center-to-center spacing (C) for a 250 micron wide projection ranges from 350 to 1,500 microns. The preferred center-to-center spacing (C) for an 800 micron wide projection ranges from 1,120 to 4,800 microns. This corresponds with a preferred width to center-to-center spacing (W:C) ratio between 1:1.4 and 1:6. In the case of the 250 micron wide projection, the more preferred W:C ratio is about 1:2. In the case of the 800 micron wide projection, the more preferred W:C ratio is about 1:1.5.

Figure 3:
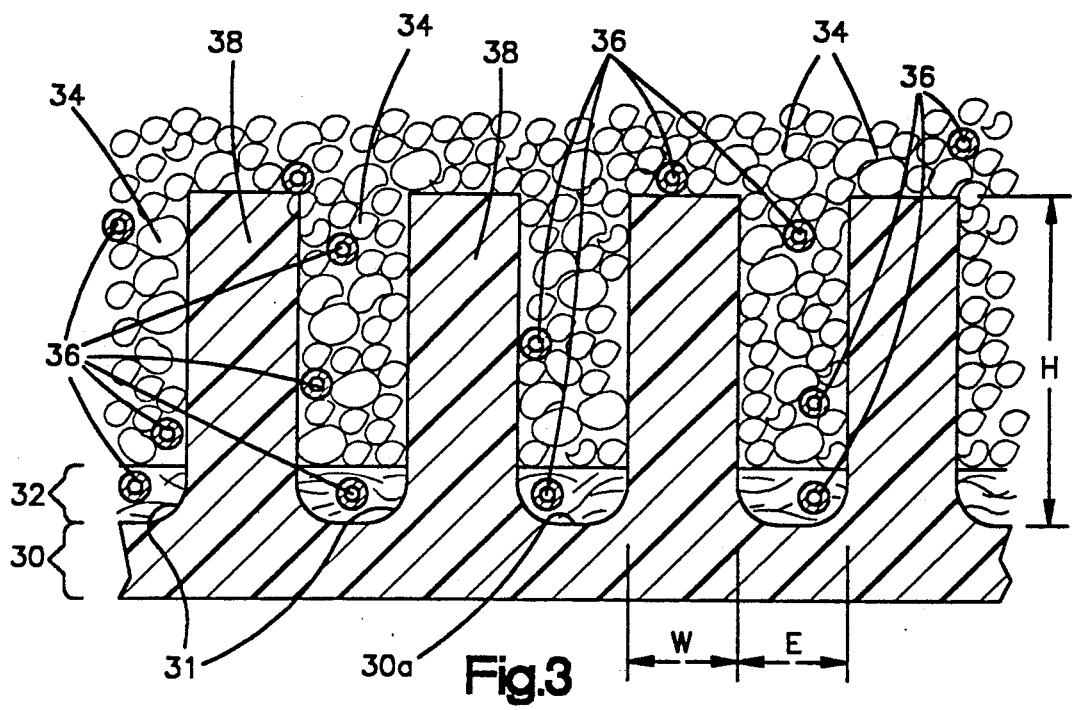
FIG. 3 is a magnified cross-sectional view taken along section line 3—3 of the tissue expander of FIG. 2, as found in vivo.

FIG. 3 illustrates the nonclassical tissue response of the body to the tissue expander 28 of the present invention. A fibrous capsule or layer 32 of collagen is comparatively thin or possibly or sometimes almost nonexistent. The fibrous capsule is scar tissue. A thin exudate or seroma layer (not shown) may be found between the fibrous capsule 32 and the outer surface 30a. The projections 38 penetrate through the fibrous capsule or collagen layer into the surrounding tissue. The volume between and above projections 38 is substantially filled with fat cells 34 and blood vessels 36. Vascularization tends to be increased. The blood vessels 36 are found very close to the outer surface 30a, including being found in the thin collagen layer 32. The thickened portion of the projection 38 near the base is shown at 31.

The presence of the projections on the surface of the tissue expander has at least three effects. First, the projections provide mechanical anchorage; that is, they penetrate into the surrounding tissue, such as fatty tissue, and hold the tissue expander in place. The tendency for sheer movement, which is a sliding movement along the interface between the tissue expander and the surrounding tissue, is reduced due to a mechanical load transfer from the tissue to the tissue expander. It is more difficult for projections to penetrate fascia or muscle tissue. In contrast, fatty tissue is far more compliant and more easily penetrated by surface projections.

Second, the projections disrupt the long range ordering of the collagen forming the fibrous capsule. The projections form transversely extending obstructions or obstacles disrupting the straight-line or long-range ordering of the collagen, as well as the orientation of blood vessels.

Third, the surface projections can disrupt the polymerization of the collagen forming the fibrous capsule. The interface between the tissue expander and the surrounding tissue is constantly irritated or through the mechanical sheer of the microstructure with the surrounding tissue, reduces the amount of collagen polymerization.

It is believed that these factors contribute substantially to the nonclassical response of a body to a tissue expander with surface projections, such as the present invention. With regard to tissue expanders, the nonclassical response is preferred, since it results in less scar tissue, a thinner capsule, and is believed to result in a reduced incidence of capsule contracture.

The dimensions of the implant projections to lessen the amount of scar tissue and minimize capsule contracture in tissue expanders have been determined by the following experimentation. The study utilized implants consisting of disks 1 cm in diameter and 1 mm thick cast from two-part silicone rubber (Dow Corning MDX4-4210). Projections, when present, consisted of a rectangular array of circular cross-section projections with the sharp edges somewhat rounded off. Projections were integrally molded on both sides of the disk.

Fifty male Sprague-Dawley rats, 250-300 gm, were utilized. Four dorsal incisions, bilateral anterior and posterior, were made. The subcutaneous plane was bluntly dissected for some distance away from the incision site and the implants inserted. One face of the disk faced outward toward the dermis; the other faced inward toward the fascia.

A total of 200 disks were implanted. Five surface morphologies and one control were tested, as follows. All dimensions are in microns.

| Projection | Width | Height | Center to Center Spacing | Edge to Edge Distance |
| --- | --- | --- | --- | --- |
| A | 100 | 500 | 200 | 100 |
| B | 250 | 750 | 500 | 250 |
| C | 400 | 1250 | 650 | 250 |
| D | 400 | 1250 | 800 | 400 |
| E | 800 | 1600 | 1200 | 400 |
| Control | 0 | 0 | N/A | N/A |

An attempt was made to distribute the different surface morphologies, including the flat disk with no surface texture as a control, equally between the four implant sites. After one month, the implants and pelts were harvested and analyzed. Each face of the disk was rated as to whether or not the animal's response to that face was nonclassical, as described above.

The implant surfaces facing the dermis showed very low rates of nonclassical response. This was not unexpected, since little adipose or fat tissue existed in the dermis. The results for the implant surfaces facing the fascia are set forth in FIG. 4.

The fascia on the posterior of the animal contained more fatty tissue than the fascia on the anterior of the animal. The posterior implants were accordingly considered more pertinent.

Figure 4:
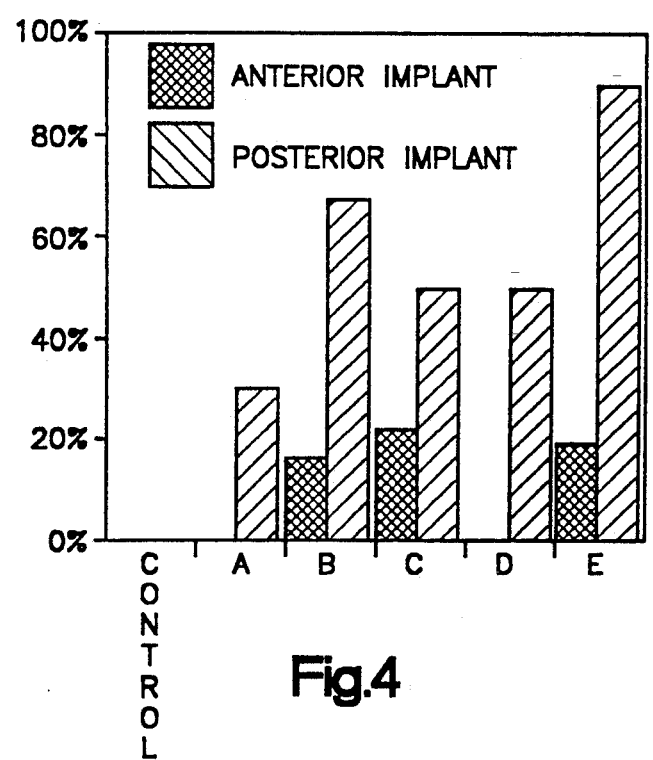
FIG. 4 is a graph illustrating the percentage of implants with selected surface morphologies which elicited a nonclassical response in a study.

It can be seen from FIG. 4 that the B morphology for posterior implants gave a significantly greater percent of nonclassical response than its nearest neighbors in terms of dimensions, those being A, C and D. The percentage nonclassical response achieved by the use of projection B morphology is more than twice that achieved by projection A and about 35% greater than that of projection C. In a similar manner, the percentage nonclassical response achieved by projection E morphology is about 80% greater than that achieved by projection D. These improvements in percentage nonclassical response are most surprising since they arise due to small differences in dimensions and such improvements are associated with disjuncted combinations of height and width dimensions.

Thus, the present inventor has found a synergistic cooperation between specific combinations of height and width projection dimensions for eliciting nonclassical tissue response in tissue expanders. The foregoing experiments are considered an appropriate model for human biologic response for tissue expanders. These specific projection dimensions are approximately 750 microns high and approximately 250 microns wide and approximately 1,600 microns high and approximately 800 microns wide. These combinations of dimensions may be used with a preferred W:E ratio between 1:0.4 and 1:5. In the case of the 250 micron wide projection, the more preferred W:E ratio is about 1:1; in the case of the 800 micron wide projection, the more preferred W:E ratio is about 1:0.5. Tissue expanders having a surface morphology in accordance with the present invention are implanted in accordance with known techniques used for implantation of tissue expanders.

An additional Example is given.

As a means of comparing the histologic response observed in animal models to that of a human, a series of five smooth tissue expanders and five tissue expanders with projections or pillars were analyzed histologically comparing the respective soft tissue response. The tissue expanders with projections ("microstructure") had projections or pillars 250 microns wide, 750 microns high, with center-to-center spacing of about 500 microns. The projections were circular in cross section, were slightly tapered with a slightly truncated cone appearance, the narrower portion being at the top. They were thickened near the base, and were arranged in a uniform array. They were uniform in size and shape. All the expanders were made of SILASTIC HP silicone elastomer and in this example all were implanted in humans. The expanders were implanted for an average of three months and were intermittently inflated from an initial size to a final size. Specimens were taken from the dome (i.e., the top), the lateral aspect (i.e., the sides) and the base (i.e., the bottom) of the implant. The analysis consisted of capsule morphology analysis and characterization of the cellular response.

The results for the smooth tissue expanders were as follows. The fibrous capsule surrounding the smooth expander was noncompliant and required either scoring (slicing) or capsulectomy in order to achieve the desired reconstructed result. The fibrous capsule surrounding the smooth tissue expander was highly aligned. The cellular response was comprised primarily of macrophages at the interface of the implant with fibroblasts and a few lymphocytes. No notable increase in the number of eosinophils, fibroblasts, mast cells, or multinucleated giant cells (MNGC's) were observed. Over the dome there was an increase in vascularity compared to the edge. Tangential sections revealed highly aligned fibers over an extended length arranged in an istropic pattern.

The results for the tissue expanders with projections were as follows. The capsule which surrounds the implant was found to be highly pliable. No difficulty in implant removal was experienced; in this regard it was similar to the control. It was apparent from microscopic examination that there was environment sensitivity, the edge response being different than the dome or the base.

Complete pillar penetration was observed for both the dome and the base extending beyond the fibrous capsule into the surrounding tissue. Where reduced mechanical pressures were noted, along the edge of the implant, associated reduction in pillar penetration was observed. MNGC's were observed in the region of the dome and not present along the edge and to a lesser extent over the base. Macrophages and fibroblasts comprised the majority of the histologic response along with eosinophils. Increased vascularity was noted in comparison to the smooth controls. In two cases seroma formation was greater than in the case of the smooth controls. Tangential sections revealed the pillars were capable of local disruption of long range ordering of the collagen fibers. The collagen fiber alignment was disrupted due to the pillars being encircled by the fibers. As a result, the collagen deposition aligned itself around each of the individual pillars and not over the entire surface of the implant. In conclusion, it was apparent the tissue expander with projections or pillars was capable of the following:

1. There was noted disruption of the long range ordering of the fibrous capsule. This in turn appeared to dramatically alter and increase the compliance and pliability of the tissues, precluding the need for scoring or capsulectomy.
2. The implants remained in place with no migration. Thus the pillars acted to reduce interfacial shear and provided implant fixation.
3. The pillars did not inhibit ease of removal nor was there any evidence of retained silicone particulates.
4. The presence of eosinophils suggested collagen remodeling was being experienced in the region of the pillar microstructure.
5. The pillars could induce neovascularization.

Microenvironment and microstructure interaction appeared to be dependent upon mechanical compressive forces having the greatest ability for penetration at the dome and base with reduced penetration on the radial aspect of the implant. The capsule at the edge was significantly thinner than the smooth control. Microstructuring could increase vascularity adjacent to the implant and the presence of pillars in this model resulted in MNGC formation which was not observed in the case of the smooth control. This suggested that the dimensions of this surface structure and its use as an expander may be jointly responsible for their presence at these early time periods.

In conclusion, the microstructure surface response in human soft tissue was analogous to that observed in the animal models. The microstructure surface, as described, enhanced the performance of the tissue expander of the present invention.

Although the preferred embodiment of this invention has been shown and described, it should be understood that various modifications, replacements, and rearrangements of the parts and methods may be resorted to without departing from the scope of the invention as disclosed and claimed herein.

What is claimed is:

1. A tissue expander having an improved nonclassical tissue response, comprising an inflatable flexible three-dimensional device, said device having a supporting structure having an outer surface, a plurality of projections extending from at least a portion of the outer surface area of the supporting structure, said plurality of projections tending to promote a nonclassical tissue response when said device is implanted in a living body and subsequently intermittently inflated to cause tissue expansion, said projections having height and width dimensions selected from the groups consisting of (1) approximately 750 microns high and approximately 250 microns wide and (2) approximately 1600 microns high and approximately 800 microns wide.

2. A tissue expander according to claim 1, wherein adjacent projections include laterally spaced surface portions, and said adjacent projections are spaced apart by a lateral spacing sized to accommodate tissue penetrated by said projections and tending to promote nonclassical tissue response.

3. A tissue expander according to claim 2, wherein said projections are uniform in size and shape.

4. A tissue expander according to claim 1, wherein the projections have a width to center-to-center spacing ratio between 1:1.4 and 1:6.

5. A tissue expander according to claim 1, wherein the projections have a width equal to approximately 250 microns and a width to center-to-center spacing ratio of approximately 1:2.

6. A tissue expander according to claim 5, wherein the projections are uniform in size and shape, are about circular in cross section, are arranged in a uniform array, extend from substantially all of the outer surface of said supporting structure, said supporting structure and said projections being formed of a medical grade silicone elastomer, at least a substantial portion of said supporting structure being stretchable.

7. A tissue expander according to claim 1, wherein the projections have a width equal to approximately 800 microns and a width to center-to-center spacing ratio of approximately 1:1.5.

8. A tissue expander according to claim 1, wherein the projections extend from substantially all of the outer surface of said supporting structure.

9. A tissue expander according to claim 1, wherein said projections are about circular in cross section, are thickened near the base, and are arranged in a uniform array.

10. A method of expanding tissue, comprising the steps of
    (a) implanting an inflatable flexible three-dimensional device in a living body beneath tissue to be expanded, said device having a supporting structure having an outer surface, a plurality of projections extending from at least a portion of the outer surface area of the supporting structure, said plurality of projections tending to promote a nonclassical tissue response when said device is implanted in a living body and subsequently intermittently inflated to cause tissue expansion, said projections having height and width dimensions selected from the groups consisting of (1) approximately 750 microns high and approximately 250 microns wide and (2) approximately 1600 microns high and approximately 800 microns wide; and
    (b) subsequently intermittently inflating said device to cause expansion of said tissue to be expanded.

11. A method according to claim 10, wherein said device is implanted in a human.

12. A method according to claim 11, wherein said subsequent intermittent inflation occurs over a two-to-six month period to progressively inflate said device.

13. A method according to claim 10, wherein adjacent projections include laterally spaced surface portions, and said adjacent projections are spaced apart by a lateral spacing sized to accommodate tissue penetrated by said projections and tending to promote nonclassical tissue response.

14. A method according to claim 13, wherein said projections are uniform in size and shape.

15. A method according to claim 10, wherein the projections have a width to center-to-center spacing ratio between 1:1.4 and 1:6.

16. A method according to claim 10, wherein the projections have a width equal to approximately 250 microns and a width to center-to-center spacing ratio of approximately 1:2.

17. A method according to claim 16, wherein the projections are uniform in size and shape, are about circular in cross section, are arranged in a uniform array, extend from substantially all of the outer surface of said supporting structure, said supporting structure and said projections being formed of a medical grade silicone elastomer, at least a substantial portion of said supporting structure being stretchable.

18. A method according to claim 10, wherein the projections have a width equal to approximately 800 microns and a width to center-to-center spacing ratio of approximately 1:1.5.

19. A method according to claim 10, wherein the projections extend from substantially all of the outer surface of said supporting structure.

20. A method according to claim 10, wherein said projections are about circular in cross section, are thickened near the base, and are arranged in a uniform array.

* * * * *